United States Patent [19]
Fischer

[11] Patent Number: 6,118,844
[45] Date of Patent: Sep. 12, 2000

[54] METHOD AND DEVICE FOR THE DETERMINATION OF MEASUREMENT UNCERTAINTIES IN X-RAY FLUORESCENCE LAYER THICKNESS

[75] Inventor: Helmut Fischer, Sindelfingen, Germany

[73] Assignee: Helmut Fischer GmbH & Co Institut für Elektronik und Messtechnik, Sindelfingen, Germany

[21] Appl. No.: 09/149,020

[22] Filed: Sep. 8, 1998

[30] Foreign Application Priority Data

Sep. 9, 1997 [DE] Germany ............... 197 39 321

[51] Int. Cl.$^7$ ..................................... G01N 23/223
[52] U.S. Cl. ........................ 378/48; 378/48; 378/50; 378/44
[58] Field of Search ................... 378/48, 50, 44; 250/207, 308

[56] References Cited

U.S. PATENT DOCUMENTS 5,029,337  7/1991  MacKenzie et al. .
5,113,421  5/1992  Gignoux et al. .
5,657,363  8/1997  Hossain et al. .
6,038,280  3/2000  Rossiger et al. .

*Primary Examiner*—David P. Porta
*Assistant Examiner*—Pamela R. Hobden
*Attorney, Agent, or Firm*—Paul Vincent

[57] ABSTRACT

In a method for the determination of the measuring uncertainty for a device for X-ray fluorescence slice thickness measurements during measurement of a layer of a sample under investigation, a spectrum S(K) simulating an actual fluorescent radiation spectrum is generated for the channels K of a spectrum and for a given thickness d of the layer and, in each channel K, a random number generator is used to repetitively accumulate a random value to construct a total number N(K) of events registered in the K-th channel in measurement time t and the standard deviation $\sigma(d)$ is determined from the spectrum of slice thicknesses d extracted by means of the repetitive random values as measure of the measurement uncertainty.

21 Claims, 3 Drawing Sheets

Fig. 3

| d Cu-thickness (μm) | normalized counting rates $x_i$ | | | | | | V |
|---|---|---|---|---|---|---|---|
| | Ni-K | | Cu-K | | Zn-K | | |
| | alpha | alpha beta | alpha | beta | alpha | beta | % |
| 0.350 | 0.676 | 0.592 | 0.015 | 0.001 | 0.029 | 0.060 | 32.9 |
| 0.631 | 0.669 | 0.589 | 0.026 | 0.002 | 0.029 | 0.055 | 19.4 |
| 1.13 | 0.665 | 0.585 | 0.045 | 0.003 | 0.028 | 0.048 | 11.1 |
| 2.04 | 0.658 | 0.579 | 0.076 | 0.005 | 0.026 | 0.037 | 7.11 |
| 3.68 | 0.649 | 0.571 | 0.125 | 0.008 | 0.023 | 0.023 | 4.72 |
| 6.61 | 0.637 | 0.560 | 0.197 | 0.013 | 0.019 | 0.010 | 3.70 |
| 11.9 | 0.625 | 0.549 | 0.299 | 0.020 | 0.013 | 0.002 | 3.72 |
| 21.4 | 0.614 | 0.539 | 0.376 | 0.027 | 0.007 | 0.000 | 5.19 |
| 38.6 | 0.608 | 0.533 | 0.436 | 0.033 | 0.002 | 0.000 | 14.1 |

METHOD AND DEVICE FOR THE DETERMINATION OF MEASUREMENT UNCERTAINTIES IN X-RAY FLUORESCENCE LAYER THICKNESS

This application claims Paris Convention Priority of German Patent application 197 39 321.1 filed Sep. 9, 1997 the complete disclosure of which is hereby incorporated by reference.

BACKGROUND OF THE INVENTION

The invention concerns a method as well as an apparatus for the determination of measurement uncertainties in a device for X-ray fluorescence layer thickness measurements for the measurement of a layer of a sample under investigation.

Devices for measuring the thickness and also the composition of layers, in particular, galvanic layers in the micrometer range but also of alloy layers using X-ray fluorescence often have X-ray tubes, a detector as well as an observation device having a focusing element. When using such a device it is necessary to determine the suitability of the apparatus for the requirements at hand. Quality control has therefore introduced the terminology "measuring means capability". Towards this end a limiting value is defined, the observance of which should guarantee the suitability of the apparatus for the application. The central question underlying this estimation of the suitability of the apparatus to be used is the precision with which a particular measuring quantity, in this case the layer thickness, can be determined using the device for X-ray fluorescence layer thickness measurements. In addition one has to determine whether or not this precision is sufficient to carry out the measurement within certain tolerances. In devices for measurement of layer thicknesses and apparatus therefor, this requirement consists of determining the measureability of certain layers or layer combinations of the sample under investigation. Towards this end at least a certain given precision must be achieved in certain thickness regions.

If the suitability of such a device has to be determined empirically each time, this would require substantial effort in particular with regard to a suitable sample material, processing time etc. In addition, for the case of new types of layer technology, such a suitable sample material is often not available at all.

For this reason certain points of departure have been used to calculate and determine the measurement uncertainty and the measuring time in such devices. Towards this end the sum of all events registered by the detector within a certain pulse height interval, described as a signal magnitude X, the measurement time t, as well as a function f describing the interdependence between the measured quantity d and the signal X are used to estimate the theoretical scatter $\sigma(d)$ in accordance with $$\sigma(d)=f'(X)*\sigma_X$$

Such a starting point is only possible if the pulse height interval considered does not overlap with interfering spectral regions during the measurement. This is however the case in complex measuring problems as well as during the measurement of a plurality of layers or alloy layers. The mutual influence of the individual layers during the fluorescence excitation leads to non-linear dependencies in the relationships between the layer thickness and counting rates X.

It is therefore the underlying purpose of the invention to create a method as well as a device of the above mentioned kind by means of which the measurement uncertainty can be determined without a comprehensive empirical experimental phase and in a reliable manner even for complicated measuring situations, such as multiple layers or alloy layers.

SUMMARY OF THE INVENTION

This purpose is solved in accordance with the invention with a method of the above mentioned kind in that a spectrum S(K), simulating the actual fluorescence radiation spectrum, is determined for the channels K of a spectrum for a given thickness d of the layer, and a Poisson-distributed random value contribution to the entire number N(K) of the events registered in the K-th channel during measurement time t is repetitively generated in each channel K using a random generator, and the standard deviation $\sigma(d)$ of the layer thicknesses obtained from the spectra generated by the repetitive random values is determined as a value for the measurement uncertainty. An apparatus according to the invention is characterized by a device to determine a spectrum simulating a fluorescence radiation spectrum, a random generator for producing a Poisson-distributed random values in the entire spectrum N(K) for the events registered in the K-th channel during measuring time t, and a unit for determining the standard deviation $\sigma(d)$ of the measurement results obtained in this fashion as a value for the measurement uncertainty.

In accordance with the invention, the measurement uncertainty, that is to say the reciprocal value of the repetition precision, of a device for fluorescence layer thickness measurements is extracted from the thicknesses d determined based on a probability distribution of events registered by the detector as the channel contents in the spectrum using the standard deviation $\sigma(d)$. Towards this end, the contents of each channel K of the spectrum are considered as individual signal quantities N which satisfy the Poisson-distribution. This so-called "natural" counting statistics directly determines the numerical results of the thickness calculation, wherein the standard deviation $\sigma(d)$ is determined for a given "fictitious" thickness d. Each simulation run leads to the determination of an average value N(K) in each channel K of a Poisson-distributed random value, so that the simulated spectrum S(K) corresponds to a single measurement. The repeated calling of such a simulation therefore permits construction of the standard deviation $\sigma(d)$ of the simulated measuring values as a reliable estimate of the desired measurement uncertainty for a given thickness d. The standard deviation, as a measurement of the scatter of the simulation events, thereby mirrors, in its reciprocal value, the repetition precision so that the actual relationships occurring during real measurements can be reliably simulated. In particular, the estimator $\sigma(d)$ extracted from the standard deviation of the individual measurements can be determined in a simple and reliable fashion over all repetitions.

An improvement provides that the simulated spectrum S K) is determined using the response function R(i,K) of the detector of a device for X-ray fluorescence layer thickness measurements for the radiation components i of the fluorescence radiation intensities of all elements of the sample with the normalized counting rate X(i) for the radiation component i in accordance with $$S(K) = \sum_i X(i) * R(i, K)$$

In this manner all values necessary for the composition of a spectrum are included.

The expression "normalized" means that the current value lies between 0 and 1 independent of the actual counting rate as seen from the relationship:

$$\frac{X_m - X_0}{X_s - X_0}$$

with $X_0 < X_m < X_s$ and $0 < X < i$ where
$X_m$=measured counting rate
$X_0$=minimum counting rate
$X_s$=maximum counting rate A response function R(i,K) is needed in the region of measurements for the numerical unfolding of the measured spectrum. It is inversely used to simulate the composition of the spectrum. The response function R is preferentially a normal distribution which, in further development, is determined through the normal distribution of the channels K of the spectrum in accordance with $$R(i, K) = A(i)/\exp(((K - B(i))/C(i))^2) +$$
$$D(i)/\exp(((K - B(i) - \text{Esc})/C(i))^2) +$$
$$E(i) + F(i) * K + G(i) * K^2 + H(i) * K^3$$

with the substantially constant parameters A–H and Esc. The response function R(i,K) is therefore a normal distribution modified with experimental corrections, wherein the constants A–K are adjusted using measured pure element spectra. Appropriate interpolation can be used such that it is not necessary to actually measure each pure element rather to extract these values from a so-called pure element library. The constant Esc describes the separation of the escape peak from the original peak in channels. In order to be able to form the spectrum S(K) as a spectral superposition of all radiative components i, the response function R(i,K) is determined for each fluorescent radiative component. If only radiative component i is incident on the detector of the device for fluorescence thickness measurement, the measured spectrum would be identical to the response function R(i,K).

The substantially constant parameters E–H preferentially describe the radiative background and can remain constant in narrow regions of fluorescence radiative energy. The parameters B are substantially proportional to the fluorescence radiation energy. The parameter C substantially describes the energy resolution of the detector and, to a good approximation, is a linear function of the fluorescence radiative energy. The escape probability D/A can, to a good approximation, be extracted directly from the pure element spectrum. At least a fraction of the substantially constant parameters A–H can be determeind by means of interpolation of the measured pure element spectra so that additional measurements of pure elements are no longer necessary.

The constant Esc is, as already mentioned, equal to the separation of the escape peak of the spectrum from the original peak, wherein the separation is equal to the difference of the peak maxima in units of channels.

In this manner, the response functions R(i,K) correspond to the actual conditions for the device for fluorescence thickness measurements through adjustment to the measured pure element spectra, and most importantly to the intensity of the primary radiation. In this manner, the spectra S(K) determined through the spectral superposition of all radiative components characterize actual applications.

In order for adjustable parameters of the device or apparatus for fluorescence thickness measurements not to have any substantial influence on the measurement uncertainty one provides that the measurement uncertainty is, in each case, determined in dependence on given measurement conditions. Adjustable parameters such as the measurement time, the measurement distance (the geometrical separation from the measuring head=collimator plus detector) and the type of radiative source (type of X-ray tube, high-voltage and anode current) are therefore defined prior to determining the measurement error and thereby prior to calculating the spectrum S(K), and are held constant. These predetermined measurement conditions can then be used to extract the normalized counting rate $(X_i)$ for the individual fluorescent radiative components of the layers of the sample under investigation. The normalized counting rates $(X_i)$ and the fluorescence radiative intensities of all elements of the sample are generally normalized to the intensities of the pure saturation thickness elements, since the detector properties then cancel out. It is thereby important to determine all $X_i$ for a defined structure of the sample under investigation with which one knows which elements are present, in which concentration, and in which layer, and for a defined apparatus type (geometry and the primary radiation).

For example, Cr/Ni/CuZn contains four elements whose K-radiative components are to be determined separately for K-α and K-β. One thereby has,
$X_{Cr-K-\alpha}$, $X_{Cr-K-\beta}$, $X_{Ni-K-\alpha}$, $X_{Ni-K-\beta}$
$X_{Cu-K-\alpha}$, $X_{Cu-K-\beta}$, $X_{Zn-K-\alpha}$, $X_{Zn-K-\beta}$.

These normalized counting rates thereby enter into determination of the associated spectrum S(K) after the response functions R(i,K) are determined for these radiative components Ni-K-α through Zn-K-β.

After the spectrum S(K) is determined, it can then be evaluated as a measured spectrum. The determination of the thickness value d is then trivial, since the evaluation step is precisely the inverse of the composition of the spectrum.

Since statistical measurement accuracy and thereby the scatter, result from the probability distribution of the events registered by the detector, an improvement provides that the probability distribution of the values determined from the random number generator in each channel K is approximated in accordance with $$W(y')dy' \sim 1/\exp(y - y'/b^2))$$

to an average value y=N(K) with N(K)=S(K) t and the distribution parameter b=sqrt (S(K)t). Each simulation run then produces an approximately Poisson-distributed random value in each channel K having an average value N(K). N(K) is thereby the entire number of events registered in the K-th channel during the measuring time. The simulated spectrum thereby corresponds to an individual measurement. The simulation run is then repeated so that the standard deviation σ(d) of the measurement results simulated in this fashion for the thickness d finally represent a reliable estimate of the desired measurement imprecision. The scatter in the simulation results mirrors the repetition precision. In this manner, the conditions, to the extent determined by a random distribution, simulate the actual relationships in a reliable and optimum manner.

It is accordingly provided that the spectrum determined by means of the random values is used to determine the layer thickness in order to be able to reliably conclude what is the measurement uncertainty for this particular layer thickness d. In an improvement the standard deviation σ(d) for differing thicknesses of the layer of a sample to be examined is determined and the standard deviation σ(d) is used in each case for each thickness d to determine a coefficient of variation V(d) in accordance with $$V(d) = \frac{\sigma(d)}{d}$$

The coefficient of variation V(d) determeind in this manner can then preferentially be compared to a given maximum coefficient of variation $V_{max}(d)$ to determine the measurement region of the device for X-ray fluorescent layer thickness measurement. The determined coefficients of variation V(d) then serve as points of interpolation for subsequent specification of the measuring region, preferentially done through interpolation of the coefficients of variation V(d). A spline method is e.g. suitable as an interpolation procedure. The measurable thicknesses determined by this measuring region can then be easily extracted.

An additional preferred configuration provides that the measurement uncertainty is determined in each case for each sample layer under investigation, since same comprises a covering layer, an intermediate layer or a plurality of intermediate layers, and a base layer of base material. In these types of multi-layer structures, all layers contribute to the individually measurable spectrum due to overlapping.

In order to be able to process and determine the extracted values in a reliable manner in each case, memory and processing units as well as at least one output unit to output the determined results are provided for.

The generation of natural counting statistics (Poisson-distribution) in each channel of the spectrum using the random number generator, and the production of differing simulations using the Monte-Carlo-method facilitate a reliable and safe determination of the statistical measuring error, that is to say the scatter, and thereby of the measuring region at differing thicknesses.

In order to begin the assignment, only the admissible maximum variation coefficient, the layer (cover layer, intermediate layers) the associated thickness of which should belong to the measuring region, the composition of the layer, as well as the adjustable parameters for the device for fluorescence layer thickness measurement are to be determined. Reference to the corresponding pure element spectra can allow, by means of the method in accordance with the invention, for determination of the measurement uncertainty as a value of the standard deviation for differing thicknesses of a layer and finally of the measuring region by extracting the coefficient of variation.

Further advantages and features of the invention can be extracted from the claims and from the following description in which an embodiment is illustrated with reference to the drawing.

BRIEF DESCRIPTION OF THE DRAWING

FIG. 3 shows a table of an embodiment with coefficients of variation V(d) extracted for differing thicknesses of the layer.

DESCRIPTION OF THE PREFERRED EMBODIMENT

Figure 1:
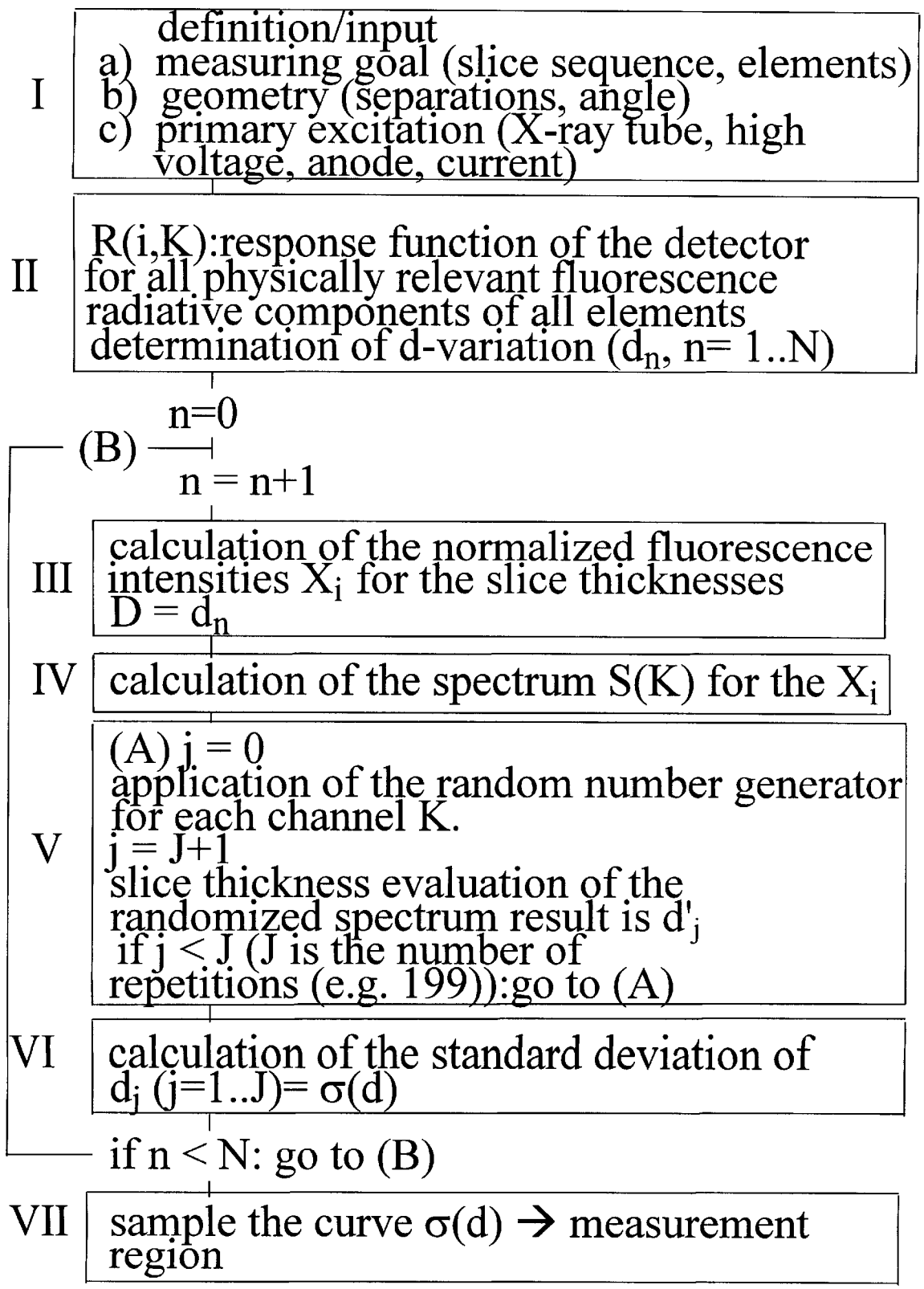
FIG. 1 shows a processing diagram of the method in accordance with the invention.

The sequence of the method of the invention in accordance with FIG. 1 is as follows:

Step I initially determines the measurement conditions such as the measuring time, excitation of the anode, operation voltage of the X-ray tube, measuring separation between detector and layer, type of filter, type of beam input as well as the beam output angle and the like. In addition, one specifies which layer (cover layer, an intermediate layer) of the sample under investigation should be used for the determination of the measurement uncertainty and thereby of the measurement region. In addition, the maximum acceptable coefficient of variation or standard deviation for the layer thickness determination is specified.

If the layer and the elements contained therein are specified, then the layer thicknesses d are identified in step II for which the standard deviation $\sigma(d)$ is to be determined and thereby, in principle, the repetition precision as the reciprocal value thereof for the measurements.

In step II the constants A–H are adjusted with the assistance of measured pure element spectra as well as through interpolation using a pure element library, and the constants Esc are determined.

In addition in step II, the response function R(i,K) of the detector for the radiation components i is determined using the constants A–H and Esc. This is done as follows $$R(i, K) = A(i) / \exp(((K - B(i)) / C(i))^2) + \\ D(i) / \exp\left(\left((K - B(i) - \text{Esc})/ C(i)\right)^2\right) + \\ E(i) + F(i) * K + G(i) * K^2 + H(i) * K^3$$

In the next step III, the fluorescence radiative intensities or the normalized counting rates X of all elements of the sample are determined, wherein they are usually determined relative to the intensities of pure saturation thickness elements so that the detector properties cancel out. The index i marks the individual physically defined radiative components.

In the subsequent step IV, the simulated spectrum is determined S(K) in accordance with $$S(K) = \sum_i X(i) * R(i, K),$$

wherein K is the channel number in the spectrum.

If only the radiation component i were incident on the detector then, as can be seen from the formula, the measured spectra would be identical to R(i, K). This formula is, in other words, the definition of the function R(i, K).

In step V, the natural counting statistics (Poisson-distribution) for a predetermined layer thickness d is simulated in each channel K using a random generator and a large number of differing simulations are produced using the Monte-Carlo-method. This means, subsequent to the determination of the spectrum S(K), each channel contents (e.g. channel 1–156) is perturbed using the random generator ("noised"). The spectrum produced in this fashion is then evaluated in the usual fashion and the value for the layer thickness d is stored for each perturbation. This is done a large number e.g. 100 of times. The average value over all experiments must then correspond to the spectral determination for the corresponding slice thickness. The standard deviation $\sigma(d)$ is then determined in step VI. In accordance with the invention, this value is an estimate of the actual statistical measurement error for a given slice thickness d.

The steps II–VI are then repeated for different given layer thicknesses having the given layer elements and/or the sample in orders, to obtain the corresponding standard deviation for differing slice thicknesses $\sigma(d)$.

Step VII determines the measurement region within which the standard deviation σ(d) should be numerically sampled for a plurality of given thicknesses d as points of interpolation using an interpolation procedure to thereby find the region of slice thicknesses d within which the standard deviation σ(d) is smaller than the maximum allowable standard deviation $\sigma_{max}(d)$. A coefficient of variation V(d) is extracted from the standard deviation in accordance with $$V(d) = \frac{\sigma(d)}{d}$$

and is compared to a maximum given coefficient of variation $V_{max}(d)$ by sampling the curve.

Figure 2:
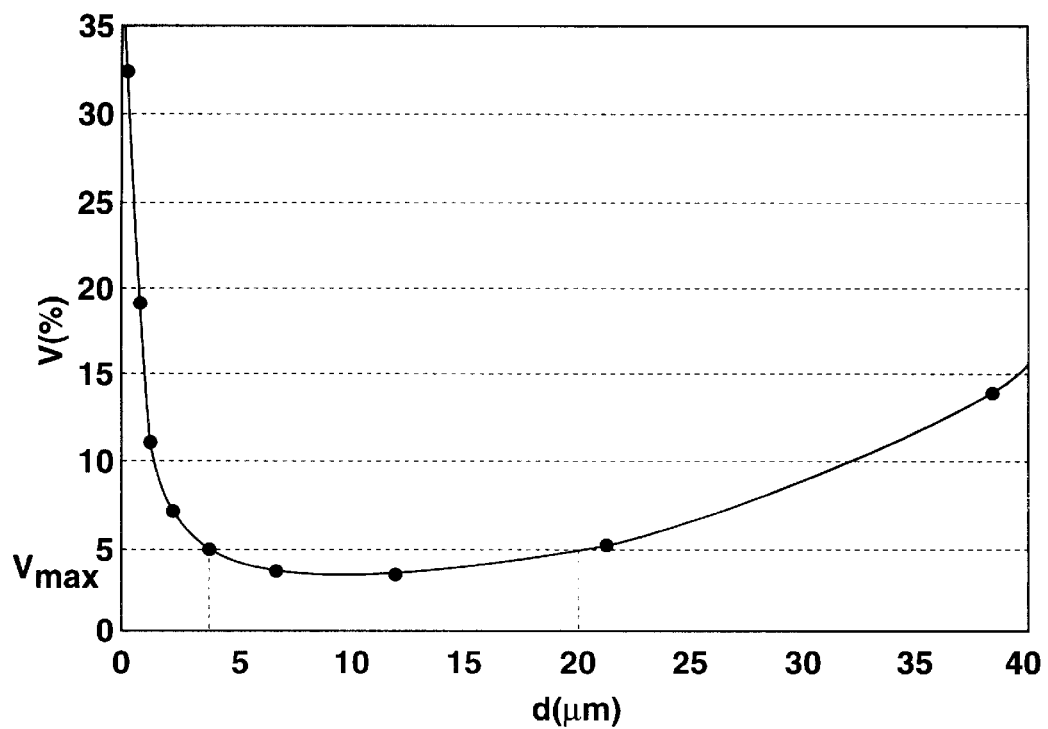
FIG. 2 shows a graphical representation of coefficients of variation V(d) of an embodiment plotted against various thicknesses.

FIG. 2 is a graphical representation of coefficients of variation V(d) in % plotted against given thicknesses d. The individual points serve as points of interpolation and are connected through interpolation using e.g. a spline procedure so that the measurement region can be easily extracted from this graph with $V_{max}(d)$ drawn therein.

In an embodiment whose results can be extracted from table 1 shown in FIG. 3 as well as from FIG. 2, the measurement region for a Cu-intermediate layer is determined with a sample having an Ni-cover layer, this Cu-intermediate layer, and a Zn base layer. The thickness of the Ni-cover layer thereby assumes a value of 10 μm. The measurement region is thereby defined by the condition V(d)<5%. As measuring conditions, a measuring time of 10 sec., a voltage of 50 kV for the X-ray tube, the use of a W-anode, filtering using a 1 mm quartz glass, a perpendicular beam input and a beam output angle of 40° are given.

Starting with these measuring conditions, the individual fluorescence radiative components (Ni-K-α, Ni-K-β, Cu-K-α, Cu-K-β, Zn-K-α, Zn-K-β) are calculated in a conventional manner. The normalized counting rates resulting thereby for these fluorescence radiative components are given in table 1.

The response function R for the specified fluorescence radiative components is then determined. In addition, the substantially constant parameter values A–H are determined from pure element measurements. One thereby assumes that the radiative background described by the parameters E–H is constant in narrow regions of fluorescence radiative energy and that the parameter B is approximately proportional to the fluorescence radiative energy with the energy resolution of the detector as selected by the parameter C being, to a good approximation, a linear function of the fluorescence radiative energy. The escape probability D/A is directly extracted from the pure element spectrum and is practically the same for the K-α and K-β components.

After the spectrum S(K) is determined for the Cu-layer thickness, each channel contents K is perturbed with the random generator. The spectrum thereby resulting, which is approximately that of the normal distribution W(y') dy', can then be analyzed in the usual fashion and the value for the Cu-thicknesses can be stored. After e.g. repeating this procedure 100 times, the average value of all experiments is determined, the standard deviation σ(d) of which provides an estimate for the actual statistical measurement error. Coefficients of variation V(d) are then determined from the standard deviations and are entered in the last column of table 1 for each of the predetermined thicknesses d.

In order to determine the measurement region, the statistical measurement errors extracted for the 13 thicknesses are connected by means of an interpolation procedure (e.g. spline method) as shown in FIG. 2. The measuring region thereby resulting having V(d)<5% can then be read-off (e.g. 3.4–21 μm thicknesses of the copper intermediate layer).

I claim:

1. A method for the determination of the measuring uncertainty in a device for X-ray fluorescence slice thickness measurements for measurement of a layer of a sample under investigation, the method comprising the steps of:
   a) determining, for a given slice thickness d, a spectrum S(K) for channels (K) of said spectrum, said spectrum approximating an actual fluorescence radiative spectrum;
   b) simulating, for each channel K, an entire number N (K) of events registered in a K-th channel within a measuring time t through repetitive use of a random Poisson-distributed generator;
   c) extracting a slice thickness d from step b);
   d) repeating steps b) and c) a plurality of times; and
   e) extracting a standard deviation σ(d) as a measure of the measurement uncertainty.

2. The method of claim 1, wherein step a) comprises the step of determining said spectrum S(K) from a response function R(i, K) of a detector of the device for X-ray fluorescence slice thickness measurements for radiative components i and for fluorescence radiative intensities of all elements of the sample with a normalized counting rate X(i) for radiative component i in accordance with $$S(K) = \sum_i X(i) * R(i, K).$$

3. The method of claim 2, wherein said response function R(i,K) comprises a normal distribution.

4. The method of claim 3, wherein the response function R(i, K) comprises a distribution of the channels K in said spectrum in accordance with $$R(i, K) = A(i)/\exp(((K - B(i))/C(i))^2) + \\ D(i)/\exp\left(\left((K - B(i) - \text{Esc})/C(i)\right)^2\right) + \\ E(i) + F(i) * K + G(i) * K^2 + H(i) * K^3$$

with substantially constant parameters A–H and Esc.

5. The method of claim 4, further comprising determining said substantially constant parameters A–H using measured spectra of pure elements.

6. The method of claim 5, wherein said substantially constant parameters E–H describe a radiative background.

7. The method of claim 5, wherein said substantially constant parameter B is approximately proportional to a fluorescence radiative energy.

8. The method of claim 5, wherein said substantially constant parameter C describes an energy resolution of said detector.

9. The method of claim 5, wherein an escape probability is given by D/A.

10. The method claim 9, wherein said substantially constant parameter Esc is equal to a separation of an escape peak of said spectrum from an original peak.

11. The method of claim 5, wherein at least one of said substantially constant parameters A–H is determined by interpolation of measured pure element spectra.

12. The method of claim 2, wherein said standard deviation σ(d) is determined in dependence on given measuring conditions.

13. The method of claim 12, wherein said normalized counting rate $X_i$ for said radiative components i of layers of the sample under investigation are determined using said given measuring conditions.

14. The method of claim 1, wherein step b) comprises the step of determining a probability distribution of values of said random generator in each channel K in accordance with $$W(y')dy' \sim 1/\exp((y-y')/b^2))$$

to a middle value y=N(K) with N(K)=S(K) t and a distribution parameter b=sqrt (S(K)t).

15. The method claim 14, wherein the slice thickness d is determined using spectra generated by said random generator.

16. The method of claim 1 further, comprising determining said standard deviation σ(d) for each of a plurality of layers in the sample.

17. The method of claims 16, further comprising extracting a coefficient of variation V(d) of differing thicknesses d of layers of the sample from said standard deviation σ(d) in accordance with $$V(d) = \frac{\sigma(d)}{d}.$$

18. The method of claim 17, further comprising comparing said coefficients of variation V(d) to a given maximum coefficient of variation $V_{max}$(d) to determine a measurement region for the device for X-ray fluorescent slice thickness measurements.

19. A device for the determination of measurement uncertainties with an apparatus for X-ray fluorescence layer thickness measurements for measurement of a layer of a sample under investigation, the device comprising:

means for determining a spectrum simulating a fluorescence radiation spectrum;

a random number generator to produce Poisson-distributed random values for an entire number N(K) of events registered in a K-th channel during measurement time t; and means for determining a standard deviation of layer thickness extracted from results obtained using said random values as a measure of the measurement uncertainty.

20. The device of claim 19, further comprising a memory unit and a processing unit.

21. The device claim 19, further comprising an output unit to output results.

* * * * *

UNITED STATES PATENT AND TRADEMARK OFFICE
CERTIFICATE OF CORRECTION

PATENT NO. : 6,118,844
DATED : September 12, 2000
INVENTOR(S) : Fischer, Helmut

It is certified that error appears in the above-identified patent and that said Letters Patent is hereby corrected as shown below:

Please replace the second line of the formula given in column 3 lines 19 through 25, column 6 lines 22 through 28 and claim 4 as follows --.

$D(i)/\exp(((K-B(i)-Esc)/C(i))^2)+$ --.

Signed and Sealed this

Twenty-sixth Day of June, 2001

Attest:

NICHOLAS P. GODICI
*Attesting Officer*     *Acting Director of the United States Patent and Trademark Office*